United States Patent [19]

Fritsche-Lang et al.

[11] Patent Number: 5,238,597

[45] Date of Patent: Aug. 24, 1993

[54] SUCROSETRICARBOXYLIC ACID AND COMPOSITIONS CONTAINING THE SAME

[75] Inventors: Wolfram Fritsche-Lang, Bensheim; Ernst I. Leupold, Neu-Anspach; Merten Schlingmann, Königstein/Taunus, all of Fed. Rep. of Germany

[73] Assignee: Hoechst Aktiengesellschaft, Frankfurt am Main, Fed. Rep. of Germany

[21] Appl. No.: 659,479

[22] Filed: Feb. 25, 1991

Related U.S. Application Data

[63] Continuation of Ser. No. 449,421, Dec. 15, 1989, abandoned, which is a continuation of Ser. No. 915,031, Oct. 3, 1986, abandoned.

[30] Foreign Application Priority Data

Oct. 7, 1985 [DE] Fed. Rep. of Germany ....... 3535720

[51] Int. Cl.$^5$ ......................... C07H 3/00; A23G 3/00; C11D 17/00
[52] U.S. Cl. ................. 252/174.18; 536/4.1; 426/658
[58] Field of Search .......... 536/1.1; 426/658; 252/174.18; 514/53

[56] References Cited

U.S. PATENT DOCUMENTS 2,845,439  7/1958  Reiners ................. 536/124
3,894,146  7/1975  Tsuyama ............... 536/4.1
3,910,880  10/1975  Lamberti ............... 536/4.1
4,108,891  8/1978  Hattori et al. ........ 260/528

OTHER PUBLICATIONS

Nieuwenhuizen et al, Polycarboxylic Acids Containing Acetal Functions: Calcium Sequestering Compounds Based on Oxidized Carbohydrates, J. An. Oil. Chem. Soc. 1983, vol. 60 pp. 120–124.
Hawley's Condensed Chemical Dictionary, p. 35.
Chemical Abstracts, vol. 98, Abstract No. 109302z.
T. A. Downey, Organic Chelating Agents, Soap and Chemical Specialties 42 (2) pp. 52–55, 105 and 106 (1966).
O. Theaner, Carbohydrate Chemistry, Pgman-Horton, vol. 1B (1980) pp. 1014 and 1015.
Ullmann's Encyklopadie der Technischen Chemie, vol. 24, p. 787 (1983).

*Primary Examiner*—Johnnie R. Brown
*Assistant Examiner*—Elli Peselel
*Attorney, Agent, or Firm*—Finnegan, Henderson, Farabow, Garrett & Dunner

[57] ABSTRACT

Sucrosetricarboxylic acid can be prepared by oxidizing sucrose with oxygen, if desired in a mixture with inert gases, by means of a more effective catalyst than platinum/alumina.

The product can be used in washing agents or as a food additive.

3 Claims, No Drawings

SUCROSETRICARBOXYLIC ACID AND COMPOSITIONS CONTAINING THE SAME

This application is a continuation of application Ser. No. 07/449,421, filed Dec. 15, 1989 now abandoned, which was a continuation of Ser. No. 06/915,031, filed Oct. 3, 1986, now abandoned.

The present invention relates to sucrosetricarboxylic acid and its secondary products such as salts, lactones, esters, amides and the like, to a process for preparing and using the same.

It is known that the catalytic oxidation of carbohydrates, specifically that of the primary hydroxymethyl groups contained therein, proceeds slowly and in most cases non-uniformly. For instance, oligomeric carbohydrates such as branched arabinoxylan from rye flour are oxidized in 4 days at 65° C. in only 4% to uronic acids. It is true that the oxidation of sucrose has also been mentioned, but statements about the isolation of the reaction products were not mentioned at the time. It was merely stated that it was found in a subsequent total hydrolysis that the hydrolyzate contained only small amounts of glucuronic acid.

The oxidation of sucrose with a platinum-alumina catalyst and oxygen has also been previously described (German Patent 886,305, Example 3 and the corresponding U.S. Pat. No. 2,845,439, Example 4). After a 6-hour treatment this oxidation gave only 60% of the theoretically expected yield of the corresponding glucuronic acid derivative. However, the isolation of this compound is not described.

The invention provides, then, sucrosetricarboxylic acid (i.e. ($\beta$-D-arabinofuranaric-2-hexulosyl)-$\alpha$-D-glucopyrano-siduronic acid) of the formula

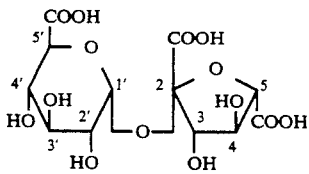

The invention further provides a process for preparing sucrosetricarboxylic acid, which comprises oxidizing sucrose with oxygen, if desired in a mixture with inert gases, for example in the form of air, by means of a significantly more effective catalyst than platinum-/alumina. Suitable catalysts are those of platinum metals, such as palladium, but in particular platinum itself, on activated carbon, in particular the more active types. These generally contain 5–10% by weight of metal, in particular platinum. In addition to a distinct increase in the rate of oxidation, an increased selectivity of the oxidation between primary and secondary hydroxyl groups of the carbohydrates, in particular of nonreducing carbohydrates, is achieved. Preferably the oxidation is carried out by treating the solid catalyst in an aqueous reaction medium with gaseous oxygen, i.e. in a three-phase reaction. This three-phase reaction is carried out for example in a bubble column reactor which can be operated not only batchwise but also continuously. In preferred embodiments, highly concentrated oxygen is used and the reaction solution is recycled, which facilitates setting, and keeping constant, the pH. It is within the capacity of the skilled worker to set the reaction solution to a selected and suitable reaction temperature and to optimize the concentration ratio of substrate/catalyst or substrate/oxygen.

The process according to the invention is generally carried out at 30° C. to the boil, preferably at 50° to 95°, in particular 60° to 90° C. In general, atmospheric pressure is employed, but it is also possible to employ superatmospheric pressure, which is a way of increasing the supply of oxygen and/or the reaction temperature. In the process according to the invention, maintaining certain sucrose concentrations is particularly advantageous; concentrations below 5% by weight easily give rise to an over-oxidation and above 20% by weight only to comparatively low conversions under atmospheric pressure. In general, pH values of 5 to 9, preferably 6 to 8, are used. The course of the reaction can be monitored by sampling, for example by means of gas chromatography analysis of the derivatized, for example silylated, products.

The sucrosetricarboxylic acid formed is generally obtained in a mixture with less oxidized intermediates, i.e. various monocarboxylic and/or dicarboxylic acids. The oxidation can be discontinued at as early a stage as a tricarboxylic content of at least 20%. However, the oxidation is generally continued until at least 30 or 40 and preferably more than 60 or 70% of sucrosetricarboxylic acid has been formed. This sucrosetricarboxylic acid can be concentrated and isolated out of the reaction mixture in a conventional manner.

The process according to the invention can be carried out, for example, in a jacketed reactor which holds the suspension of the catalyst in the aqueous medium and which contains at the bottom a frit or another correspondingly suitable porous membrane and through which a gas stream, very finely divided by this separating membrane, flows from the underside. For economic and safety reasons, the oxygen is expediently passed through the reaction medium at such a rate that the catalytically activated oxygen is just consumed at the upper end of the bubble column. To improve the degree of mixing and to prolong the time of exposure to the oxygen, it can be advantageous to stir the reaction mixture.

On account of its chemical structure or structural elements, the sucrosetricarboxylic acid formed is suitable as such or in the form of its immediately obtainable reaction products, i.e. in particular mixtures with the intermediates, for applications in the field of complexing agents, for example analogously to gluconic acid and glucaric acid in washing agent formulations, as food additives, for example for the applications customary for citric acid, as a polyfunctional reactant (crosslinking) and also as a starting material for chemical reactions (hydrophilizing reagent).

The process according to the invention has made it possible to carry out the oxidation of sucrose in such a way as to form the hitherto unknown sucrosetricarboxylic acid.

EXAMPLES

1) In an externally heated, upright glass tube (diameter: 50 mm, length: 80 cm) having a frit bottom and, installed at a point slightly thereabove, a discharge means for the reaction mixture, a stream of oxygen (about 25 liters (S.T.P.)/h) flows upwardly through a solution of 120 g of sucrose in 1.2 liters of water and also 60 g of added platinum catalyst (5% of Pt/active carbon). The acids formed by the oxidation are wholly or partly converted into the sodium salts either by feeding in sodium hydroxide solution, with the attendant possibility of pH control, or by means of the corresponding molar amounts of initially introduced sodium hydrogencarbonate. At a temperature of 80° C. in the oxidation and neutralization and a pH of 6.5 held constant during both stages, the products have after silylation and according to gas chromatography analysis the following compositions as a function of the reaction time (see Table 1):

TABLE 1

Composition of oxidation products as a function of reaction time (in percent)

|  | 6 h | 12 h | 18 h |
|---|---|---|---|
| Sucrose | consumed | — | —. |
| Monocarboxylic acids (2 isomers) | 20.9 | 5.2 | 1.5 |
| Dicarboxylic acids (2 isomers) | 38.9 | 39.6 | 29.7 |
| Tricarboxylic acid I | 5.1 | 22.3 | 35.3 |

The reaction solution is filtered to remove the catalyst, and the filtrate is concentrated in a thin film evaporator and freeze-dried. Yield 104 g (86.7% by weight). The total acid content is 7.18 mEq/g (theoretical value for sucrosetricarboxylic acid 7.80 mEq/g).

To characterize the sucrosetricarboxylic acid (STA), the reaction mixture is converted by means of commercially available cation exchanger into the free acids and freeze-dried after filtration. After complete acetylation with an excess of acetic anhydride and equimolar amounts of p-toluenesulfonic acid (20° C., 20 h), the sirupy residue is chromatographed over silica gel (eluent: methylene chloride/methanol 10:1 v.v.). The pentaacetylated sucrosetricarboxylic acid obtained last with polar eluent in the chromatography is converted with catalytic amounts of sodium methanolate in methanol into the trisodium salt.

$^1$H-NMR (D$_2$O, 400 MHz): $\delta = 5.45$ (d,H-1',$J_{1',2'}=3.75$ Hz), 4.23–4.12 (m, H-5',H-3,H-4,H-5), 3.82, (struct. t, H-3'), $J_{3',4'}=9.5$ Hz, $J_{2',3'}=9.8$ Hz), 3.54 (dd, H-2', $J_{1',2'}=3.75$ Hz, $J_{2',3'}=9.8$ Hz), 3.45 (struct. t,H-4',$J_{3',4'}=J_{4',5'}=9.5$ Hz).

GC-MS (gas chromatography/mass spectroscopy) (after silylation, chemical ionization with isobutane) m/z=961 (M+1-fragment of the 8-fold silylated compound, relative intensity about 0.1%).

FAB-MS (fast atom bombardment) (sodium salt used, glycerol as matrix) m/z=451 (MH+, relative intensity 36%).

2) By the method of Example 1, 120 g of sucrose, dissolved in 1.2 liters of water, are oxidized at 60° C. and pH 7.5 in a stream of oxygen. Table 2 shows the compositions determined by GC analysis.

TABLE 2

Composition of oxidation products as a function of reaction time (in percent)

|  | 8 h | 28 h | 52 h | 84 h |
|---|---|---|---|---|
| Sucrose | 1.1 | — | — | — |
| Monocarboxylic acids (2 isomers) | 28.9 | 10.3 | 5.7 | 4.7 |
| Dicarboxylic acids (2 isomers) | 35.8 | 36.1 | 27.3 | 23.0 |
| Oxalic acid | 5.9 | 10.8 | 12.6 | 10.9 |
| Tricarboxylic acid I | 4.6 | 20.7 | 32.7 | 40.9 |

Filtration to remove the catalyst and freeze-drying the filtrate leaves 93.8 g (78.0% by weight).

We claim:
1. The compound β-D-arabinofuranaric-2-hexulosyl-α-D-glucopyranosiduronic acid or the sodium salt thereof.
2. A food composition containing, as an additive, an effective amount of a compound as claimed in claim 1.
3. A washing formulation containing, as an additive, an effective amount of a compound as claimed in claim 1.

* * * * *